United States Patent [19]
Bezwada et al.

[11] Patent Number: 4,653,497
[45] Date of Patent: Mar. 31, 1987

[54] CRYSTALLINE P-DIOXANONE/GLYCOLIDE COPOLYMERS AND SURGICAL DEVICES MADE THEREFROM

[75] Inventors: Rao S. Bezwada, Whitehouse Station; Shalaby W. Shalaby, Lebanon; Hugh D. Newman, Jr., Chester, all of N.J.

[73] Assignee: Ethicon, Inc., Somerville, N.J.

[21] Appl. No.: 802,547

[22] Filed: Nov. 29, 1985

[51] Int. Cl.4 .................... A61L 17/00; C08G 63/08
[52] U.S. Cl. .................. 128/335.5; 525/411; 525/415; 525/937; 528/354; 528/357
[58] Field of Search ............... 128/335.5; 525/411, 525/415; 528/354

[56] References Cited

U.S. PATENT DOCUMENTS

| | | | |
|---|---|---|---|
| 4,052,988 | 10/1977 | Doddi et al. | 528/354 |
| 4,137,921 | 2/1979 | Okuzumi et al. | 525/411 X |
| 4,157,437 | 6/1979 | Okuzumi et al. | 525/415 X |
| 4,243,775 | 1/1981 | Rosenaft et al. | 528/354 X |
| 4,300,565 | 11/1981 | Rosenaft et al. | 525/415 X |
| 4,470,416 | 9/1984 | Kafrawy et al. | 528/354 X |
| 4,591,630 | 5/1986 | Gertzman et al. | 528/354 X |

*Primary Examiner*—Earl Nielsen
*Attorney, Agent, or Firm*—Charles J. Metz

[57] ABSTRACT

Copolymers are made by reacting glycolide with a mixture of p-dioxanone monomer and homopolymer. The copolymers are useful in making surgical devices such as surgical sutures.

16 Claims, No Drawings

CRYSTALLINE P-DIOXANONE/GLYCOLIDE COPOLYMERS AND SURGICAL DEVICES MADE THEREFROM

The invention relates to crystalline copolymers of p-dioxanone and glycolide, a process for making said copolymers, and to surgical devices such as high compliance, rapid absorbing monofilament sutures and ligatures made therefrom.

BACKGROUND OF THE INVENTION

Surgical devices, in particular absorbable monofilament sutures and ligatures and hemostatic ligating clips, made from p-dioxanone homopolymer are valuable commercial articles. This invention is directed to a means for providing p-dioxanone polymers that have properties that are different from those that can be obtained in the homopolymer. This invention thereby provides a means for extending the utility of p-dioxanone polymers.

P-dioxanone polymers are disclosed by Doddi et al. in U.S. Pat. No. 4,052,988, who also disclose and claim sutures and other surgical devices made from such polymers. In the paragraph bridging Columns 8 and 9 of the Doddi et al. patent, it is disclosed that glycolide may be copolymerized with p-dioxanone to produce absorbable sutures.

Surgical filaments such as sutures and ligatures of p-dioxanone homopolymer are commercially available in the form of monofilaments. One of the desirable characteristics of a monofilament suture is to exhibit a combination of high strength (in the form of straight tensile and knot tensile strength) and good compliance or pliability. Surgical filaments of p-dioxanone homopolymer are perceived by surgeons as being rather stiff and wiry. One of the valuable advantages of this invention is that it provides p-dioxanone polymers that are more pliable than p-dioxanone homopolymer, thereby substantially enhancing the utility of p-dioxanone polymers.

BRIEF SUMMARY OF THE INVENTION

The polymers of the invention are certain crystalline copolymers of p-dioxanone and glycolide that combines the fast absorbing characteristics of high glycolide polymers with the much better pliability of poly(p-dioxanone). The invention also provides sterilizable surgical devices made from these copolymers, preferably monofilament sutures and ligatures that have a desirable combination of good strength, fast absorption, and excellent pliability (as exhibited by low Young's modulus). Other useful surgical devices that are provided by the invention include components of surgical staples, tubular structures such as fine diameter sheaths for nerve and small vessel anastomoses, and fabrics including woven or knitted tubular structures.

The invention also provides a process for producing the copolymers of the invention which comprises:

adding glycolide to a mixture of p-dioxanone homopolymer and p-dioxanone monomer and subjecting the resulting reaction mixture to an elevated temperature for a period of time sufficient to produce a copolymer of p-dioxanone and glycolide.

THE PRIOR ART

In addition to the Doddi et al. patent cited above (which is considered by Applicants to be the most relevant prior art), a number of other patents are relevant in that they disclose the production of absorbable copolymers by the sequential addition of monomers. These patents include Okuzumi et al., U.S. Pat. Nos. 4,137,921 and 4,157,437 and Rosensaft et al., U.S. Pat. Nos. 4,243,775 and 4,300,565.

DETAILED DESCRIPTION OF THE INVENTION

The most convenient way to carry out the process of the invention is to first carry out the melt polymerization of p-dioxanone monomer to produce a mixture of poly(p-dioxanone) homopolymer and p-dioxanone monomer, and to then use this mixture in the reaction with glycolide. This homopolymerization is carried out in the presence of a catalytically effective amount of a suitable metal-containing catalyst such as stannous octoate. Typical proportions of catalysts are found in monomer:catalyst molar ratios of from about 10,000:1 to about 60,000:1, and preferably from about 15,000:1 to about 40,000:1. The polymerization is carried out in the presence of an initiator such as an alkanol, a glycol, a hydroxyacid, or an amine. Specific illustrations of such initiators include 1-dodecanol, diethylene glycol, glycolic acid, lactic acid, ethanolamine, and the like. Typical proportions of the initiator are found in monomer:initiator molar ratios of from about 500:1 to about 1800:1. The polymerization of p-dioxanone is carried out at elevated temperatures under an inert atmosphere for a period of time sufficient to produce a mixture of p-dioxanone homopolymer and p-dioxanone monomer. Typical polymerization reaction temperatures are within the range of from about 100° C. to about 130° C., and is preferably about 110° C. The polymerization reaction is carried out until an equilibrium is reached between polymer and monomer. This is usually attained at about 15 to 30 weight percent monomer, based on weight of monomer plus polymer. Depending on the temperature, this reaction usually takes from about 4 to about 8 hours. At the preferred temperature of about 110° C., the usual reaction time is 5 to 6 hours.

The next step is to add glycolide to the mixture of p-dioxanone homopolymer and monomer, and to subject the resulting reaction mixture to elevated temperature for a period of time sufficient to produce the segmented copolymers of the invention. As a general rule, the reaction temperature for this polymerization will be within the range of from about 120° C. to about 180° C., and preferably from 120° C. to 150° C. At reaction temperatures within this range, the polymerization will be complete within a period of from about 1 to about 4 hours.

The proportion of glycolide that is added to the mixture of p-dioxanone homopolymer and monomer is usually from about 3 to about 25 weight percent, and preferably from about 5 to about 20 weight percent, based on total weight of the reaction mixture (i.e., total weight of glycolide, p-dioxanone homopolymer, and p-dioxanone monomer).

The Examples below illustrate the production of the copolymers of the invention.

EXAMPLE 1

Preparation of Polydioxanone-melt/glycolide at 95/5 initial weight composition (95.6/4.4 by mole %)

A flame dried, 250 milliliter, round bottom, two-neck flask was charged under nitrogen with 95 grams (0.9306 mole) of p-dioxanone, 0.266 milliliter of 1-dodecanol, and 0.0984 milliliter of stannous octoate (0.33 molar solution in toluene). The contents of the reaction flask were held under high vacuum at room temperature for about 16 hours. The flask was fitted with a flame dried mechanical stirrer and an adaptor with a hose connection. The reactor was purged with nitrogen three times before being vented with nitrogen. The reaction mixture was heated to 110° C. and maintained there for 5 hours. A sample of this polymer was removed (I.V.=1.21 dl/g) and 5 grams (0.04308 mol) of glycolide was added. The temperature was raised to 140° C. over the next 15 minutes, and maintained there for 1 hour. The temperature of the oil bath was lowered to 90° C. and maintained there for about 65 hours. The polymer was isolated, ground, and dried 48 hours/80° C./0.1 mm Hg to remove any unreacted monomer. A weight loss of 13.7% was observed. The resulting polymer had a melting range of 96°–100° C. by hot stage microscopy and an inherent viscosity ("IV") of 1.63 dl/g. Unless otherwise stated, all inherent viscosities reported herein were determined at 25° C. and a concentration of 0.1 g/dl in hexafluoroisopropyl alcohol.

EXAMPLE 2

Preparation of Polydioxanone-melt/glycolide at 90/10 initial weight composition (91/9 by mole %)

A flame dried, 250 milliliter, round bottom, two-neck flask was charged under nitrogen with 90 grams (0.8816 mole) of p-dioxanone, 0.26 milliliter of 1-dodecanol, and 0.098 milliliter of stannous octoate (0.33 molar solution in toluene). The contents of the reaction flask were held under high vacuum at room temperature for about 16 hours. The flask was fitted with a flame dried mechanical stirrer and an adaptor with a hose connection. The reaction mixture was heated to 110° C. under a stream of nitrogen, and maintained there for 5 hours. A sample of this polymer was removed and 10 grams (0.0862 mole) of glycolide was added. The temperature was raised to 160° C. over the next 10 minutes, and maintained there for 1 hour. The temperature of the oil bath was lowered to 85° C. and maintained there for about 65 hours. The polymer was isolated, ground, and dried 48 hours/80° C./0.1 mm Hg to remove any unreacted monomer. A weight loss of 13.8% was observed. The resulting polymer had a melting range (by hot stage microscopy) of 100°–105° C., an inherent viscosity of 1.44 dl/g. at 25° C., a $T_g$ (by DSC) of −8° C., a $T_m$ (by DSC) of 97° C., a crystallinity (by X-ray diffraction) of 45%, and a PDO/PG molar ratio of 87.3/12.7 by NMR. (The PDO/PG molar ratio is the ratio of polymerized p-dioxanone to co-polymerized glycolide in the polymer. A mole of glycolide contains two glycolic acid units).

EXAMPLE 3

Preparation of Polydioxanone-melt/glycolide at 80/20 initial weight composition (82/18 by mole %)

A flame dried, 250 milliliter, round bottom, two-neck flask was charged under nitrogen with 80 grams (0.7836 mole) of p-dioxanone, 0.217 milliliter of 1-dodecanol, and 0.048 milliliter of stannous octoate (0.33 molar solution in toluene). The contents of the reaction flask were held under high vacuum at room temperature for about 16 hours. The flask was fitted with a flame dried mechanical stirrer and an adaptor with a hose connection. The reaction mixture was heated to 110° C. under a stream of nitrogen, and maintained there for 5 hours. A sample of this polymer was removed and 20 grams (0.1723 mole) of glycolide was added. The temperature was raised to 140° C. and maintained there for 1 hour. The temperature of the oil bath was raised to 160° C. over the next 10 minutes, and maintained there for about 40 minutes. The polymer was isolated, ground, and dried 48 hours/80° C./0.1 mm Hg to remove any unreacted monomer. A weight loss of 6.4% was observed. The resulting polymer had a melting range by hot stage microscopy of 95°–100° C., an inherent viscosity of 1.64 dl/g, and a crystallinity of 40%. By DSC, the $T_g$ was −2° C. and the $T_m$ was 125° C., with a suggestion of a second $T_m$ at 193° C. The PDO/PG molar ratio was found to be 82.7/17.3 by NMR.

Extrusion

In the preparation of fibers, especially surgical filaments, the copolymers are melt extruded through a spinnerette in a conventional manner to form one or more filaments, in accordance with the following general procedure:

Extrusion of the copolymers described herein was accomplished using an INSTRON Capillary Rheometer. The copolymers were packed in the preheated (80° to 90° C.) extrusion chamber and extruded through a 40 mil die (L/D=24.1) after a dwell time of 9 to 12 minutes at the extrusion temperature and a ram speed of 2 cm/min. While extrusion temperatures depend both on the polymer Tm and on the melt viscosity of the material at a given temperature, extrusion of the subject copolymers at temperatures of about 10° to 75° C. above the Tm is usually satisfactory. The extrusion temperatures of the example copolymers described herein ranged from 120° to 205° C.

The extrudate was typically taken up through an ice water quench bath at 24 feet/minute, although other bath temperatures and take-up speeds were occasionally used. A screw-type extruder or similar device can be substituted for the INSTRON Capillary Rheometer.

The extrudate filaments are subsequently drawn about 6X to 7X in a one or multistage drawing process in order to achieve molecular orientation and improve tensile properties. The manner of drawing is as follows:

The extrudate (diameter range, 16–20 mils) is passed through rollers at an input speed of four feet per minute and into a heated draw bath of glycerine. The temperatures of the draw bath can vary from about 25° to 90° C.; the examples described herein employ temperatures between 49° and 58° C. The draw ratio in this first stage of drawing can vary from 3X to about 7X; the examples described herein employ first stage draw ratios from 4X to 5.5X.

The partially drawn fibers are then placed over a second set of rollers into a glycerine bath (second stage) kept at temperatures ranging from 50° to 95° C.; the examples described herein employ second stage draw temperatures of 70° to 75° C. Draw ratios of up to 2X are applied in this second stage, but a ratio range of from 1.2X to 1.6X was employed in the examples. The fiber is passed through a water-wash, taken up on a spool, and dried. A set of hot rollers can be substituted for a portion or all of the glycerine draw bath. The resulting oriented filaments have good straight and knot tensile strengths.

Dimensional stability and in vivo tensile strength retention of the oriented filaments may be enhanced by subjecting the filaments to an annealing treatment. This optional treatment consists of heating the drawn filaments to a temperature of from about 40° to 90° C., most preferably from about 60° to 80° C. while restraining the filaments to prevent any substantial shrinkage. This process may begin with the filaments initially under tension or with up to 20% shrinkage allowed prior to restraint. The filaments are held at the annealing temperature for a few seconds to several days or longer depending on the temperature and processing conditions. In general, annealing at 60° to 80° C. for up to about 24 hours is satisfactory for the copolymers of the invention. Optimum annealing time and temperature for maximum fiber in vivo strength retention and dimensional stability is readily determined by simple experimentation for each fiber composition.

The filaments thus produced may be fabricated into sutures or ligatures, attached to surgical needles, packaged, and sterilized by known techniques.

The characteristic properties of the filaments of the invention are readily determined by conventional test procedures. The tensile properties (i.e., straight and knot tensile strengths, Young's Modulus, and elongation) displayed herein were determined with an INSTRON tensile tester. The settings used to determine the straight tensile, knot tensile, break elongation, and Young's Modulus were the following, unless indicated:

|  | Gauge Length (cm) | Chart Speed (cm/min) | Crosshead Speed (cm/min) |
|---|---|---|---|
| Straight Tensile | 12 | 20 | 10 |
| Knot Tensile | 5 | 10 | 10 |
| Break Elongation | 12 | 20 | 10 |
| Young's Modulus | 12 | 20 | 10 |

The straight tensile strength is calculated by dividing the force to break by the initial cross-sectional area of the fiber. The elongation at break is read directly from the stress-strain curve of the sample allotting 4-1/6% per centimeter of horizontal displacement.

Young's Modulus is calculated from the slope of the stress-strain curve of the sample in the linear elastic region as follows:

$$\text{Young's Modulus} = \frac{\tan\theta \times GL \times CS \times SL}{XH \times XS}$$

$\theta$ is the angle between the slope and the horizontal, XS is the initial cross-sectional area of the fiber, SL is the scale load, XH is the crosshead speed, CS is the chart speed, and GL is the gauge length. The SL may be selected to provide a $\theta$ close to 45°.

The knot tensile strength of a fiber is determined in separate experiments. The test article is tied into a surgeon's knot with one turn of the filament around flexible tubing of ¼ inch inside diameter and 1/16 inch wall thickness. The surgeon's knot is a square knot in which the free end is first passed twice, instead of once, through the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

The tensile strength values and Young's modulus (Y.M.) are reported as KPSI, or $PSI \times 10^3$.

EXAMPLES 4-6

The copolymers described in Examples 1 to 3 were extruded into monofilament fibers. The orientation conditions are shown in Table I and the tensile properties of these copolymers are summarized in Table II.

TABLE I

| ORIENTATION CONDITIONS | | | | |
|---|---|---|---|---|
| Copolymer Example No. | Fiber Example No. | 1st Stage Draw | 2nd Stage Draw | Overall Draw Ratio |
| 1 | 4 | 4X (58° C.) | 1,562X (75° C.) | 6.25X |
| 2 | 5 | 5X (52° C.) | 1.3X (72° C.) | 6.5X |
| 3 | 6 | 5X (50° C.) | 1.2X (71° C.) | 6X |

TABLE II

| Copolymer Example No. | Example 1 | Example 2 | Example 3 |
|---|---|---|---|
| Initial PDO/PG Weight Ratio | 95/5 | 90/10 | 80/20 |
| PROPERTIES OF ORIENTED FIBERS | | | |
| Fiber Example No. | Example 4 | Example 5 | Example 6 |
| Str. Tensile, KPSI | 88 | 87 | 65 |
| Knot Tensile, KPSI | 53 | 49 | 43 |
| Elongation % | 49 | 61 | 94 |
| Y. M., KPSI | 211 | 143 | 81 |
| Annealed | 12 hr/ 60° C.[2] | 12 hr/ 60° C. | 12 hr/ 60° C. |
| Str. Tensile, KPSI | 79 | 85 | 61 |
| Knot Tensile, KPSI | 50 | 62 | 51 |
| Elongation % | 34 | 39 | 55 |
| Y. M., KPSI | 281 | 283 | 201 |
| In Vitro BSR[1] 4 Days/50° C. | 79% | 49% | 43% |

[1] Breaking strength retention-percentage of original straight tensile strength after the indicated number of days in phosphate buffer (pH = 7.26) at the indicated temperature.
[2] No shrinkage

EXAMPLE 7

Preparation of Polydioxanone-melt/glycolide at 90/10 initial weight composition (91/9 by mole %) using diethylene glycol as an initiator A flame dried, 250 milliliter, round bottom, two-neck flask was charged under nitrogen with 90 grams (0.8816 mole) of p-dioxanone, 0.055 milliliter of diethylene glycol, and 0.098 milliliter of stannous octoate (0.33 molar solution in toluene). The contents of the reaction flask were held under high vacuum at room temperature for about 16 hours. The flask was fitted with a flame dried mechanical stirrer and an adaptor with a hose connection. The reaction mixture was heated to 110° C. under a stream of nitrogen and maintained there for 5 hours. A sample of this polymer was removed (I.V. 1.16 dl/g) and 10 grams (0.0862 mol) of glycolide was added. The temperature was raised to 160° .C. over the next 10 minutes, and maintained there for 1 hour. The temperature of the oil bath was lowered to 85° C. and maintained there for about 65 hours. The polymer was isolated, ground, and dried 48 hours/80° C./0.1 mm Hg to remove any unreacted monomer. A weight loss of 16.8% was observed. The resulting polymer had a melting range of 94°-99° C. by hot stage microscopy and an inherent viscosity of 1.88 dl/g.

EXAMPLE 8

The copolymer of Example 7 was melt-extruded through a spinneret in a conventional manner. The resulting extrudate was drawn 6.5X in two stages (5X @ 52° C.; 1.3X @ 72° C.), and annealed 12 hours at 60° C. with no shrinkage. The physical properties of the annealed monofilaments were:

| | |
|---|---|
| Straight Tensile, KPSI | 88 |
| Knot Tensile, KPSI | 55 |
| Elongation % | 30% |
| Young's Modulus, KPSI | 204 |
| In Vitro BSR | 34% |
| 4 days/50° C./7.27 pH | |

EXAMPLES 9 AND 10

Preparation of Polydioxanone-melt/glycolide at 90/10 initial weight composition.

A thoroughly dried, mechanically stirred 1.5 gallon stainless steel reactor was charged with 1800 grams (17.632 moles) of p-dioxanone, 3.96 milliliters of 1-dodecanol, and 1.955 milliliters of stannous octoate (0.33 molar solution in toluene). The contents of the reactor were held under high vacuum at room temperature for about 16 hours. The reactor was purged and vented with nitrogen. The reaction mixture was heated to 110° C. and maintained there for about 6 hours. A sample of the polymer was removed and 200 grams (1.723 mole) of glycolide was added. The temperature was raised and maintained at 140°-150° C. for about 45 minutes in Example 9, whereas, in Example 10, the temperature was raised to about 120° C. and maintained there about 1 hour. The polymers were isolated, ground and dried to remove unreacted monomers. Polymer and fiber properties of these Examples are shown below in Table III. The extruded fiber of Example 9 was drawn 7X (5X @ 49° C., then 1.4X @ 72° C.) and the extruded fiber of Example 10 was drawn 6.75X (5X @ 53° C., 1.35X @ 70° C.).

TABLE III

| | Polydioxanone-melt/glycolide | |
|---|---|---|
| Polymer Properties | Example 9 (Natural)[3] | Example 10 (Natural) |
| I.V., dl/g | 1.77 | 1.82 |
| M.P. (Hot Stage Microscopy) | 102° C. | 98–102° C. |

| Fiber Properties | Oriented | Annealed 12 h/60° C. | Oriented | Annealed 12 h/60° C. |
|---|---|---|---|---|
| Diameter, (mils) | 7.8 | 8.1 | 7.5 | 7.8 |
| Str. Tensile, KPSI | 106 | 89 | 100 | 86 |
| Knot Tensile, KPSI | 48 | 48 | 51 | 53 |
| Elongation @ Break, % | 60 | 30 | 63 | 48 |
| Young's Modulus, KPSI | 134 | 192 | 121 | 221 |
| In Vitro BSR[4] | | | | |
| 4 days/50° C. | — | 57% | — | 55% |
| 7 days/50° C. | — | — | — | 34% |
| In Vivo BSR[5] | | | | |
| 3 Weeks | — | 28% | — | 30% |
| 4 Weeks | — | 17% | — | 12% |
| In Vivo Absorption[6] | | | | |
| 91 days | — | 21% | — | 23% |
| 119 days | — | 0 | — | 0 |
| 154 days | — | 0 | — | 0 |

[3]"Natural" means undyed.
[4]In Vitro BSR - Percent of original straight tensile strength remaining after the indicated number of days in phosphate buffer, pH = 7.26, at 50° C.
[5] [6]In vivo BSR and absorption analysis procedures are explained below.

Breaking Strength Retention In Vivo

The breaking strength retention (BSR) in vivo of a fiber is determined by implanting two strands of the fiber in the dorsal subcutis of each of a number of Long-Evans rats. The number of rats used is a function of the number of implantation periods, employing 4 rats per period giving a total of eight (8) examples of each of the periods. Thus 16, 24, or 32 segments of each fiber are implanted corresponding to two, three, or four implantation periods. The periods of in vivo residence are 7, 14, 21, or 28 days. The ratio of the mean value of 8 determinations of the breaking strength (determined with an INSTRON tensile tester employing the following settings: a gauge length of 1 inch, a chart speed of 1 inch/minute, and a crosshead speed of 1 inch/minute) at each period to the mean value (of 8 determinations) obtained for the fiber prior to implantation constitutes its breaking strength retention for that period.

In Vivo Absorption

The in vivo absorption test is carried out as follows:
Two 2-centimeter sections of the sample filaments are implanted into both the left and right gluteal muscles of two female rats for each period of the study. This procedure yields a potential total of 8 cross-sections per period, for periods of 5, 91, 119, 154 and 210 days.

The implants are recovered at the designated intervals and fixed in buffered formalin. Muscle cross-sections are made and stained with H&E and examined microscopically. Tissue reactions are evaluated, and the diameter of the remaining filament is determined. The filament diameter after 5 days is used as the 100% reference point for determining the percent cross sectional area remaining after the later periods.

EXAMPLE 11

Preparation of Polydioxanone-melt/glycolide at 90/10 initial weight composition (91.1/8.9 mole %) in Pilot Plant Size Reactor A thoroughly dried mechanically stirred 10-gallon stainless steel helicone reactor was charged, under nitrogen purge, with 10,050 grams (98.529 moles) of p-dioxanone, 10.95 milliliters of stannous octoate catalyst solution (0.33 molar in toluene), 15.13 grams of 1-dodecanol, and 11.16 grams of D&C Violet #2 dye. The contents of the reactor were held under a vacuum of 1 mm of mercury, or lower, for 20 minutes. The vacuum was released with dry nitrogen and the contents were again subjected to a vacuum of at least 1 mm or mercury for an additional 20 minutes. The reactor was purged with nitrogen. The reaction mixture was heated to 110° C. Polymerization time was six hours from the time the reaction mixture reached 100° C. At the end of the six-hour first stage polymerization period (IV=1.23 dl/g, unreacted monomer=22.8%), 1117 grams (9.629 moles) of glycolide was added under nitrogen purge to the reactor. The temperature was raised to and held at about 145° C. for ¾ hour. The polymer was isolated, ground, sieved, and then dried in a one cubic foot vacuum tumble drier for ten hours at ambient temperature, then for 32 hours at 70° C., followed by a four-hour cool down period, to remove unreacted monomer. A summary of the polymer properties is presented in Table IV.

TABLE IV

| I.V. | 2.18 dl/g |
|---|---|
| Tg (DSC) | −5° C. |
| Tm (DSC) | 112° C. |
| Crystallinity (X-ray) | 33% |
| PDO/PG Mol ratio (by NMR) | 86.3/13.7 |

EXAMPLE 12

The copolymer of Example 11 was extruded into monofilaments by melting the copolymer at 130°–160° C. and pumping the melt through a 60 mil capillary possessing a 5/1 length to diameter ratio. The extrudate was quenched by passage through a water bath and then was drawn in two stages on rolls. First stage drawing was done on rolls at room temperature, and the second drawing through a heated oven. Some of the processing conditions of Example 14 are shown below:

| Block/Die temp., (°C.) | 145/139 |
|---|---|
| 1st-Godet speed, (fpm) | 13 |
| Total draw ratio | 5.4X |
| Oven temperature, (°C.) | 68 |
| Crystallization time, (mins.) | 7–8 |

The fiber was allowed to crystallize over night at room temperature and then was redrawn in one stage through a heated oven. After redrawing, samples were annealed under nitogen for six hours with 0% relaxation at 90° C.

The physical properties of size 2/0 Example 12 fibers are shown below, compared with typical properties of a similarly sized commercial dyed p-dioxanone homopolymer monofilament (PDO) control.

TABLE V

|  | Example 12 | PDO Control |
|---|---|---|
| Diameter (mils) | 13.8 | 13.7 |
| Str. Tensile, PSI | 86,000 | 77,000 |
| Knot Tensile, PSI | 46,000 | 44,000 |
| Elongation, % | 45 | 29 |
| Young's Modulus | 181,000 | 250,000 |

The copolymers of this invention comprise long sequences of polymerized p-dioxanone covalently bonded to copolymeric chains of polymerized p-dioxanone and glycolide. NMR analyses of the copolymers confirm that the comonomers are covalently linked. X-ray analyses of the copolymers indicate the presence of crystallinity of one or more of the comonomer species. It also indicates the presence of long enough segments of one monomeric species to give rise to crystallinity. These two techniques support the view that the copolymers of this invention are not random copolymers (random copolymers are normally essentially non-crystalline.) Gel permeation chromatography data shows that the copolymers of the invention have only one molecular weight distribution curve, and are therefore not blends of two or more distinct polymers.

Drawn and oriented filaments made from the copolymers of this invention exhibit the relatively rapid In vivo absorption characteristics of filaments made from polymers having a high content of polymerized glycolide (although the copolymers of this invention contain only a minor proportion of polymerized glycolide). However, the filaments of this invention are much more pliable than are filaments made from high glycolide content polymers. Therefore, the filaments of this invention can be used as surgical sutures and ligatures in monofilament form; they do not need to be braided. To illustrate this feature, filaments made from glycolide homopolymer or 90/10 glycolide/lactide copolymer usually have Young's modulus values of the order of $2 \times 10^6$, whereas the drawn and oriented filaments made from the preferred copolymers of this invention have Young's modulus values below about $3 \times 10^5$, an order of magnitude lower.

As a comparison, in Vivo BSR of size 4/0 monofilaments prepared from the copolymers of Examples 9 and 10, annealed 12 hours at 60 C. With no relaxation, are compared with the in Vivo BSR of size 4/0 braided 90/10 glycolide/lactide copolymer in Table VI:

TABLE VI

|  | Example 9 | Example 10 | 90/10 PG/PL* Braid |
|---|---|---|---|
| Base Line, lbs. | 4.2 | 4.0 | 5.5 |
| % BSR, 3 weeks | 28 | 30 | 29 |
| % BSR, 4 weeks | 17 | 12 | 5 |

*Typical values

The copolymers of the invention may be characterized as follows:

Contain from 75 to 97 weight percent polymerized p-dioxanone, the remainder being polymerized glycolide. For the preferred surgical filament utility, the copolymers contain from about 90 to 97 mol percent polymerized p-dioxanone, the remainder being polymerized glycolide;

In the natural (undyed) state, the copolymers have melting points of from about 90° to 125° C., by hot stage microscopy. (The addition of dye may raise the melting point by as much as 5° C.)

In the molten state, by optical microscopy, the copolymers have a single phase;

By X-ray diffraction analysis, the copolymers have a crystallinity of from about 25 to 50%;

By gel permeation chromatography, the copolymers of this invention show only a single peak in the molecular weight distribution curve; and I.V. values of from 1.6 to 2.6 dl/g.

The properties of monofilaments produced from the copolymers of the invention are dependent upon a number of factors, including the PDO/PG mol ratio, the copolymerization conditions, the drawing and annealing conditions, the molecular weight, and the size of the filament. As a general rule, drawn and annealed filament made from the preferred copolymers (which have PDO/PG mol ratios of 90/10 to 97/3), will have the following properties:

| Straight Tensile, KPSI | 70–120 |
|---|---|
| Knot Tensile, KPSI | 40–80 |
| Elongation, % | 25–60 |
| Young's Modulus, KPSI | 150–300 |

-continued

| In Vivo BSR, % | |
|---|---|
| 3 weeks | 20–50% |
| 4 weeks | 10–30% |
| In Vivo absorption, to zero | less than 4 to 5 months |

What is claimed is:

1. Process for producing a crystalline copolymer of p-dioxanone and glycolide which comprises subjecting a mixture of p-dioxanone homopolymer, p-dioxanone monomer, and glycolide to an elevated temperature for a period of time sufficient to produce a crystalline copolymer of p-dioxanone and glycolide.

2. Process of claim 1 which comprises the steps of:
   (a) polymerizing p-dioxanone monomer in the presence of a catalytically effective amount of a polymerization catalyst and an initiator to produce a first mixture of p-dioxanone homopolymer and p-dioxanone monomer; and
   (b) adding glycolide to said first mixture to produce a second mixture, and subjecting said second mixture to an elevated temperature for a period of time sufficient to produce a copolymer of p-dioxanone and glycolide.

3. The process of claim 2 wherein said first mixture contains from 15 to 30 weight percent p-dioxanone monomer, based on total weight of said first mixture.

4. The process of claim 2 wherein the glycolide is employed in an amount of from about 3 to about 25 weight percent, based on total weight of p-dioxanone and glycolide charged in steps (a) and (b).

5. The process of claim 2 wherein step (b) is carried out at a temperature within the range of from about 120° to about 180° C.

6. A crystalline copolymer of p-dioxanone and glycolide produced by the process of claim 1.

7. A crystalline copolymer of p-dioxanone and glycolide produced by the process of claim 2.

8. A crystalline copolymer of p-dioxanone and glycolide produced by the process of claim 3.

9. A crystalline copolymer of p-dioxanone and glycolide containing from about 3 to about 30 weight percent polymerized glycolide, the remainder being polymerized p-dioxanone, said copolymer being characterized as follows:

An inherent viscosity of 1.6 to 2.6 dl/g;
A melting temperature of 90° to 125° C. by hot stage microscopy;
A crystallinity of 25 to 50%;
A single peak in the molecular weight distribution curve; and
Single phase in the molten state.

10. The crystalline copolymer of claim 9 containing from 90 to 97 mol percent polymerized p-dioxanone, the remainder being polymerized glycolide.

11. A drawn and oriented filament comprising the segmented copolymer of claim 10.

12. The filament of claim 11 in the form of a monofilament.

13. The filament of claim 12 in the form of a sterile surgical suture.

14. The monofilament of claim 12 having the following properties:

| Straight Tensile, KPSI | 70–120 |
|---|---|
| Knot Tensile, KPSI | 40–80 |
| Elongation, % | 25–60 |
| Young's Modulus, KPSI | 150–300 |
| In Vivo BSR, % | |
| 3 weeks | 20–50% |
| 4 weeks | 10–30% |
| In Vivo Absorption, to zero | less than 4 to 5 months |

15. The sterile surgical suture of claim 13 attached to a needle.

16. A surgical device comprising the copolymer of claim 9.

* * * * *